United States Patent
Kim et al.

(10) Patent No.: US 10,317,409 B2
(45) Date of Patent: Jun. 11, 2019

(54) GLYCOSYLATION SITE-SPECIFIC ANTIBODIES AND ANTI-CANCER COMPOUNDS

(71) Applicants: Hyesook Kim, Bloomfield Hills, MI (US); Sohee Kim, Seoul (KR)

(72) Inventors: Hyesook Kim, Bloomfield Hills, MI (US); Sohee Kim, Seoul (KR)

(73) Assignee: Detroit R&D, Inc., Detroit, MI (US)

( * ) Notice: Subject to any disclaimer, the term of this patent is extended or adjusted under 35 U.S.C. 154(b) by 397 days.

(21) Appl. No.: 14/195,209

(22) Filed: Mar. 3, 2014

(65) Prior Publication Data

US 2014/0296167 A1 Oct. 2, 2014

Related U.S. Application Data

(60) Provisional application No. 61/771,588, filed on Mar. 1, 2013.

(51) Int. Cl.

| | | |
|---|---|---|
| *G01N 33/53* | (2006.01) | |
| *G01N 33/574* | (2006.01) | |
| *A61K 31/496* | (2006.01) | |
| *A61K 31/7076* | (2006.01) | |
| *G01N 33/50* | (2006.01) | |
| *A61K 31/433* | (2006.01) | |

(52) U.S. Cl.
CPC ..... *G01N 33/57496* (2013.01); *A61K 31/496* (2013.01); *A61K 31/7076* (2013.01); *G01N 33/5011* (2013.01); *G01N 33/5091* (2013.01); *G01N 33/57415* (2013.01); *G01N 33/57419* (2013.01); *G01N 33/57423* (2013.01); *G01N 33/57438* (2013.01); *A61K 31/433* (2013.01); *G01N 2400/02* (2013.01)

(58) Field of Classification Search
CPC ......... G01N 2500/00; G01N 33/57415; G01N 33/57423; G01N 33/57438; G01N 33/57496; G01N 33/5091; G01N 33/5011; G01N 33/57419; G01N 2400/02; A61K 31/433
See application file for complete search history.

(56) References Cited

PUBLICATIONS

Kamemura et al., (The Journal of Biological Chemistry, vol. 277, No. 21, Issue of May 24, pp. 19229-19235, 2002).*
Rudikoff et al (Proc Natl Acad Sci USA 1982 vol. 79 p. 1979).*
Harlow & Lane ( "Antibodies: A Laboratory Manual" (1988) Cold Spring Harbor Laboratory Press, Cold Spring Harbor, New York, pp. 25-26).*

* cited by examiner

*Primary Examiner* — Julie Wu
*Assistant Examiner* — Carmencita M Belei
(74) *Attorney, Agent, or Firm* — Kohn & Associates, PLLC (57) ABSTRACT

A method of characterizing the protein O-GlcNAcylation site-specificity of an antibody. A method of detecting or quantitating the expression of site-specific O-GlcNAcylated proteins expressed in cells and biological samples. A method of diagnosing cancer in a host based on the cellular expression of site-specific O-GlcNAcylated proteins. A method of screening anti-cancer compounds according to their ability to increase a level O-GlcNAcylation of oncogene or tumor suppressor proteins. Methods of treating cancer in an animal host by administering compounds that increase a level of O-GlcNAcylated c-myc or p53 in cancer cells. A method of distinguishing subclasses of pancreatic cancer according to the sensitivity of pancreatic cancer cells to an imidazole derivative, and a method of personalized pancreatic cancer treatment delivered according to the sensitivity subclasses.

7 Claims, 7 Drawing Sheets

GLYCOSYLATION SITE-SPECIFIC ANTIBODIES AND ANTI-CANCER COMPOUNDS

GOVERNMENT SUPPORT

Research in this application was supported, in part, by contracts from National Cancer Institute (NCI Contract HHSN261201100073C).

BACKGROUND OF THE INVENTION

1. Technical Field

The invention relates to the characterization of site-specific antibodies for O-GlcNAcylated proteins, and for the use of the characterized antibodies for the detection of O-GlcNAcylated proteins in biological systems, the screening of drugs that modulate protein O-GlcNAcylation, and the diagnosis and treatment of cancer.

2. Background Art

O-GlcNAcylation (N-acetylglucosamine modification) of nuclear and cytosol proteins regulates many cell functions. O-GlcNAcylation of proteins plays a critical role in cell cycle regulation, apoptosis and signal transduction. Modification of O-GlcNAcylation of proteins by O-GlcNAc transferase (OTG) (synthesis of O-GlcNAcylated protein) is reversible by the activity of O-GlcNAc hydrolase (O-GlcNAcase) (cleavage of an O-GlcNAc moiety of protein). The addition and removal of the O-GlcNAc moiety to serine (Ser) or threonine (Thr) regulate the function of proteins directly or via decreased phosphorylation of the same or nearby Ser and Thr residues, and are related to diabetes and cancer (1).

O-GlcNAcylated proteins play a critical role in physiology and in diseases including cancer. High O-GlcNAcase activity results in low O-GlcNAcylation of a critical site of a protein. Low O-GlcNAcylation of a critical site of an oncoprotein or tumor suppressor protein can increase phosphorylation at or near that site, and can thereby induce or promote cancer cell proliferation and/or metastasis.

Over 120 O-GlcNAcylated nuclear and cytosolic human proteins have been found in mammals. They include seven nuclear pore proteins, thirty-one transcription factors, six RNA-binding proteins, seven phosphatases, kinases and adapter proteins, twenty-nine cytoskeletal proteins, five chaperones, seven metabolic enzymes, other regulatory proteins and six viral proteins (2).

Contrary to the known consensus sequence of N-glycosylation, Asn-X-Ser/Thr (X=any amino acid except for Pro), the O-GlcNAcylation consensus sequence is not known. Most Ser/Thr sites for O-GlcNAcylation are on or near to phosphorylation sites. O-GlcNAcylation of a site prevents phosphorylation at the site or a site close to the O-GlcNAcylation site, reversing phosphorylation-dependent cellular function of the molecule. The converse mechanism also operates, with phosphorylation at or near a O-GlcNAcylation site preventing O-GlcNAcylation.

O-GlcNAcylation of a protein is carried out by activity of O-GlcNAc transferase using UDP-GlcNAc. O-GlcNAcylation can be reversed by activity of O-GlcNAcase. A single O-GlcNAcase gene, evolutionarily conserved from bacteria to has been found to carry out all O-GlcNAcase activity.

In contrast to the numerous phosphatases that regulate various critical cell functions including cell survival, proliferation and metastasis, only one O-GlcNAcase regulates the removal of an O-GlcNAc moiety from numerous proteins, and thereby regulate increased or decreased functions of cellular proteins. This fact strongly suggests that activity of the O-GlcNAcase depends on its substrate, which is an O-GlcNAcylation site (target amino acid sequence) unique to each protein. There is therefore a need for O-GlcNAcylation site-specific antibodies to detect the unique O-GlcNAcylation site characteristic of each protein.

Pan-specific antibodies for O-GlcNAcylation, which recognize only the O-GlcNAc moiety common to all O-GlcNAcylated protein cannot be used for identification of an O-GlcNAcylated target protein in Western blot analysis and immunohistochemistry (IHC). Even in immunoprecipitation (IP) assay, accuracy of the result depends on the capture antibodies. Even when the capture antibodies bind to the target proteins, the pan-specific antibodies for O-GlcNAcylation cannot distinguish the target O-GlcNAcylation site from other O-GlcNAcylation sites of the protein with differential cellular function.

There are multiple O-GlcNAcylated sites for each oncoprotein or tumor suppressor protein, whereas only one or two sites are involved with cancer cell proliferation and/or metastasis. It has been reported that the O-GlcNAcylation site of c-myc is Thr-58 (T58) and the counteracting phosphorylation sites are T58, Ser-62 (S62) and Ser-71 (S71) (3). The O-GlcNAcylation site of p53 has been reported to be Ser-149 (S149) and the counteracting phosphorylation site as Thr-155 (T155) (4).

For example, T58 of c-myc protein, a mutational hot spot in lymphomas, is a site for both phosphorylation and O-GlcNAcylation, which induce ubiquitin-dependent degradation and increased stability, respectively. T58/S62 phosphorylation of c-myc protein also decreases T58 GlcNAcylation (5,6). Another example is p53 tumor suppressor protein. Phosporylation of the p53 at T155 induces ubiquitin-dependent degradation, which decreases p53 levels, whereas GlcNAcylation of p53 at S149 prevents p53 degradation and stabilizes p53 proteins (4). Accumulation of the p53 protein is beneficial. Its role in cell growth-arrest and apoptosis in response to DNA damage protects cells from uncontrolled proliferation, which occurs in cancer cells. The need for O-GlcNAcylation site-specific antibodies for c-myc and p53 is therefore especially acute.

Inhibitors of GlcNAcase activity have been screened using bacterial and human recombinant GlcNAcases by measurement of a decreased fluorescent signal of the fluorescent substrate of GlcNAcase, 4-methylumbelliferol (4-MU)-GlcNAc, (pseudo substrate) which is cleaved by the enzyme resulting in a loss of fluorescent signal (7). This method can only identify inhibitors of GlcNAcase that inhibit 4-MU-GlcNAc cleavage. As previously stated, the specificity of O-GlcNAcase depends on the target O-GlcNAcylation site of a protein. A compound found to inhibit the cleavage of 4-MU-GlcNAc is therefore not necessarily an inhibitor of the action of O-GlcNAcase upon specific proteins, such as, p53 and c-myc. Thus, O-GlcNAcase inhibitors have to be screened using an actual O-GlcNAcylated protein as a substrate. This type of screening requires detection by site-specific antibodies. This is another reason why there is a need for O-GlcNAcylation site-specific antibodies to detect the unique O-GlcNAcylation site characteristic of each protein.

SUMMARY OF INVENTION

The present invention provides a method of characterizing the protein O-GlcNAcylation site specificity of an antibody. The method selects O-GlcNAcylation site-specific antibodies that recognize proteins on the basis of a specific O-GlcNAcylation site, and that discriminate between the O-GlcNAcylated and unmodified forms of the O-GlcNAcylation site. The present invention also provides a method of detecting or quantitating the expression of a site-specific O-GlcNAcylated protein in cells and biological samples, using the selected O-GlcNAcylation site-specific antibodies. The present invention further provides a method of diagnosing the presence of cancer in an animal host, by quantitating site-specific O-GlcNAcylation of oncogenes and tumor suppressor genes, in immunoassays with the O-GlcNAcylation site-specific antibodies. The present invention still further provides a method for screening a candidate drug for anticancer activity, based on its effect on the O-GlcNAcylation of oncogenes and tumor suppressor genes. The present invention also provides methods of treating cancer in an animal host by administering an anti-cancer compound selected on the basis of its ability to increase the O-GlcNAcylation of c-myc or the O-GlcNAcylation of p53. The present invention further provides a method of combination therapy of cancer, using a combination of compounds that increase the O-GlcNAcylation of c-myc and the O-GlcNAcylation of p53. The present invention still further provides methods for distinguishing subclasses of pancreatic cancer on the basis of sensitivity to an imidazole derivative. The present invention also provides a method of personalized pancreatic cancer therapy based on the sensitivity of a patient's pancreatic cancer to an imidazole derivative.

DESCRIPTION OF THE DRAWINGS

Other advantages of the present invention will be readily appreciated as the same becomes better understood by reference to the following detailed description when considered in connection with the accompanying drawings wherein:

FIGS. 2A and 2B show Western blots showing specificity of antibodies for O-GlcNAcylated and corresponding unmodified c-myc and p53 proteins; Panel A shows a Western blot analyses of BSA conjugated with c-myc and p53 peptides, with and without O-GlcNAcylation, using peptide-antigen affinity purified antibodies diluted 5,000-fold, to assess specificity of antibodies produced by immunization of rabbits; Panel B shows Western blot analyses of BSA conjugated with O-GlcNAcylated c-myc and p53 peptides to be used for monoclonal antibody production using polyclonal antibodies for O-GlcNAcylated c-myc and p53 diluted 5,000-fold; Panel A, Peptide #1-G, 16-mer, Peptide #2-G, 9-mer and Peptide #4-G, 6-mer synthetic c-myc target peptides containing O-GlcNAcylated Thr-58 and Peptide #1-N, 16-mer and Peptide #2-N, 9-mer synthetic target c-myc peptides containing corresponding unmodified Thr-58 and Panel B, peptide #1-G, 10-mer p53 peptide containing O-GlcNAcylated Ser-149, Lane 1, BSA (2 µg), Lane 2, BSA-O-GlcNAc p53 peptides (0.2 µg); Lane 3, BSA-O-GlcNAc c-myc peptides (0.2 µg); BSA polymers were formed during peptide conjugation;

FIGS. 6A-6C show an analysis of GlcNAcylated c-myc levels: Panel A, O-GlcNAcylated c-myc levels in MCF-7 (Lanes 1 through 4) and MCF10A (Lanes 5 through 8) cells after treatment of the cells for 4 hr with 1% DMSO (Lanes 1 and 5), an O-GlcNAcase inhibitor, acetazolamide (Lanes 2 and 6), an O-GlcNAcase inhibitor, N6-methyladenosine 5'-monophosphate (Lanes 3 and 7) and medium (control) (Lanes 4 and 8); Western blot analysis (8-16% gel) was carried out with cell lysates (20 µg/lane) using antibodies for O-GlcNAcylated c-myc (Peptide #1-G, 5,000-fold diluted); the inhibitor was dissolved in DMSO (final concentration in media, 1%); O-GlcNAcylated c-myc is marked with an arrow; Panels B and C show increased O-GlcNAcylated c-myc levels after treatment of MCF-7 cells for 4 hr with 2 mM O-GlcNAcase inhibitor, ketoconazole; Panel B: Western blot analysis was carried out with nuclear lysates (20 µg/lane) using antibodies for O-GlcNAcylated c-myc (Peptide #2-G, 5,000-fold diluted); the inhibitors were dissolved in DMSO (final concentration in media, 1%); Lane 1, medium (control), Lane 2, 1% DMSO; Lane 3, buspirone; and Lane 4, ketoconazole; O-GlcNAcylated c-myc is marked with an arrow; Panel C: Western blot analysis was carried out with nuclear lysates (20 µg/lane) using antibodies for O-GlcNAcylated c-myc (Peptide #1-G, 5,000-fold diluted); the inhibitors were dissolved in DMSO (final concentration in media, 1%); Lane 1, 1% DMSO; Lane 2, ketoconazole; O-GlcNAcylated c-myc is marked with an arrow;

FIGS. 7A and 7B are show electrophoretic analyses of showing O-GlcNAcylated p53 levels.

the inhibitor was dissolved in DMSO (final concentration in media, 1%); O-GlcNAcylated p53 is marked with an arrow; FIGS. 8A and 8B are graphs showing cell proliferation (FIG. 8A) and data and photographs from cell invasion assays (FIG. 8B)

DETAILED DESCRIPTION OF THE INVENTION

The present invention includes a method of characterizing the protein O-GlcNAcylation site specificity of a candidate antibody, that is, of determining whether a candidate antibody is a site-specific antibody. The term "site-specific antibody" refers to an antibody that binds specifically to an O-GlcNAcylatable site of a protein or peptide only if that site is O-GlcNAcylated. The term also refers to an antibody that binds to the same O-GlcNAcylatable site only if that site is unmodified, that is, not O-GlcNAcylated. In contrast, pan-specific antibodies for O-GlcNAcylation recognize only a O-GlcNAc moiety common to many or all O-GlcNAcylated proteins. The term "site-specific antibody" can indicate either a plurality of site-specific antibody species with a defined site specificity, such as the affinity purified or unpurified antiserum of an immunized animal, or a single antibody species, such as a monoclonal antibody secreted into a culture supernatant or an ascites fluid.

An O-GlcNAcylatable site of a protein or peptide is referred to herein as a target site, and a protein or peptide containing a target site is termed a target protein or target peptide. Because target sites are characterized by specific amino acid sequences, the term "target sequence" is used synonymously with "target site".

Candidate site-specific antibodies are preferably generated by immunizing an animal against a defined antigenic peptide of an O-GlcNAcylatable protein. The defined peptide includes a target site containing a Ser or Thr residue, and optionally includes a plurality of flanking amino acids on at least one side of the target site. To generate a candidate site-specific antibody for an O-GlcNAcylated target protein, the Ser or Thr of the peptide antigen is O-GlcNAcylated. To generate a candidate site-specific antibody for an unmodified target protein, the Ser or Thr of the peptide antigen is not O-GlcNAcylated. The defined peptide antigens can be synthetic, recombinant, or produced by the fragmentation of a whole natural or recombinant protein. Less desirably, candidate site-specific antibodies can be generated by immunizing an animal against a whole recombinant or natural O-GlcNAcylatable protein, although this method is expected to have little success. The site-specific antibodies employed in the methods of the present invention are generated by immunization with defined peptides, and are commercially available, for example from Detroit R&D, Detroit, Mich.

The antibody characterization method of the present invention includes the steps of providing four proteins or peptides thereof. Two of the proteins are target proteins, that is, proteins including the target site against which the specificity of the candidate antibody is tested. One of the target proteins is O-GlcNAcylated at the target site. Alternatively a peptide of the protein, also O-GlcNAcylated at the target site, can be provided. The other target protein is the corresponding unmodified target protein (or peptide), that is, the same protein target protein lacking O-GlcNAcylation at the target site.

Two of the proteins are site-specificity control proteins, that is, proteins or peptides that have a different O-GlcNAcylation site than the target protein. The different O-GlcNAcylation site is termed a non-target site. One of the site-specificity control proteins is an O-GlcNAcylation site-specificity control protein or peptide, that is O-GlcNAcylated at the non-target site. The other site-specificity control protein is the corresponding unmodified site-specificity control protein or peptide, that is, the same protein or peptide lacking O-GlcNAcylation at the non-target site.

In the ensuing steps of the method, two candidate antibodies are each assayed for reactivity with target proteins (or peptides, depending on the case), and with site-specificity control proteins (or peptides). If a candidate antibody reacts specifically with the O-GlcNAcylated target protein or peptide, does not cross-react with the corresponding unmodified target protein or peptide, and does not cross-react with the O-GlcNAcylation site-specificity control protein or peptide, then the candidate antibody has been determined to be a site-specific antibody to the O-GlcNAcylated target protein or peptide. That is, it can distinguish the O-GlcNAcylated form of the target protein from the corresponding unmodified target protein, and site-specifically distinguish the target protein from any other O-GlcNAcylated proteins.

Similarly, if the candidate antibody to the unmodified target protein reacts specifically with the corresponding unmodified target protein or peptide, and does not cross-react with the O-GlcNAcylated target protein or peptide; and does not cross-react with the corresponding unmodified site-specificity control protein or peptide; then the candidate antibody has been determined to be a site-specific antibody to unmodified target protein or peptide.

In Examples 1 and 2, the site-specificity and sensitivity of candidate antibodies against the O-GlcNAcylated and unmodified forms of c-myc and p53 were characterized. Candidate antibodies to the target O-GlcNAcylated myc peptide were generated against a peptide in which Thr-48 was which was in GlcNAcylated form (e.g. peptide 2G).

Candidate antibodies to the unmodified c-myc peptide were generated against a peptide in which Thr-48 was unmodified (e.g. peptide 2N).

The candidate antibodies were both tested for reactivity against peptides conjugated to BSA. The peptides included an O-GlcNAcylated c-myc peptide, as the O-GlcNAcylated target peptide; the unmodified form of the same peptide, as the unmodified target peptide; an O-GlcNAcylated p53 peptide as the GlcNAcylation site-specificity control peptide; and the unmodified form of the same p53 peptide as the unmodified site-specificity control peptide.

Figure 2:
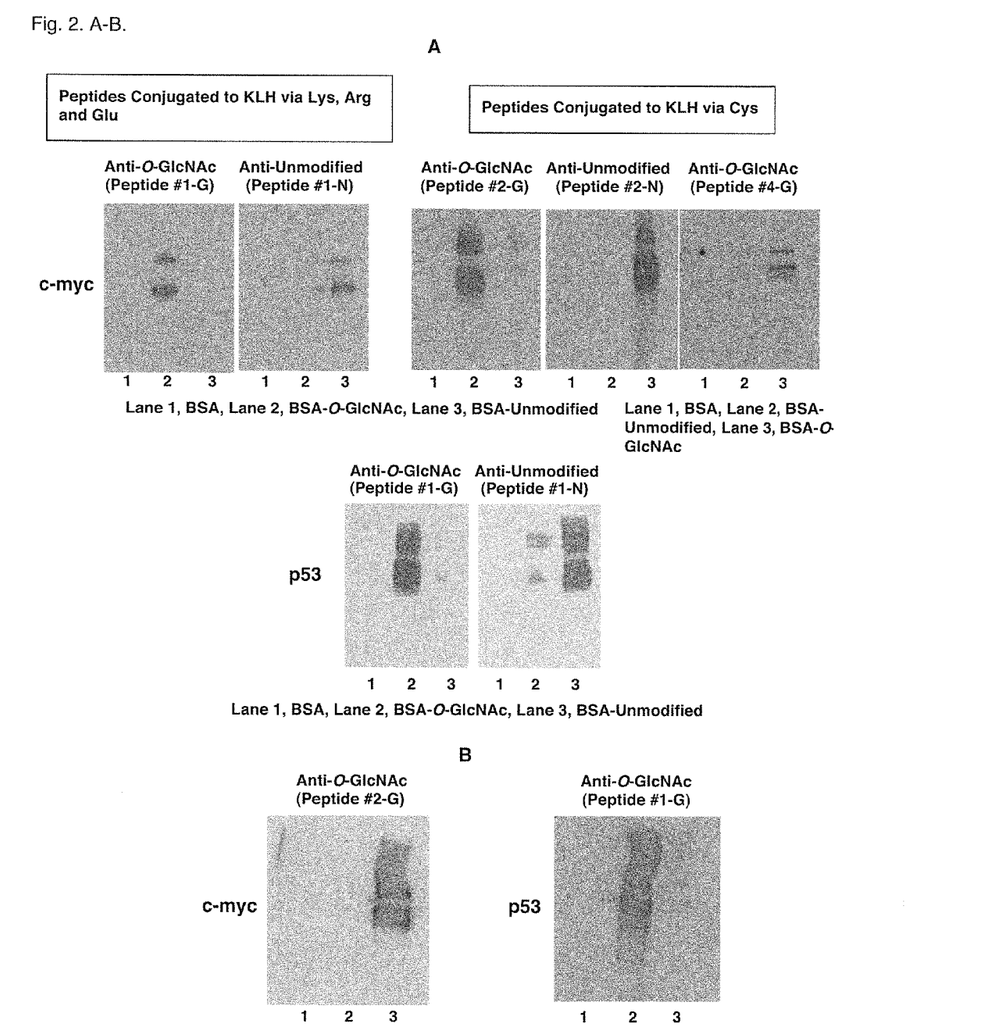

In an experiment of Example 2, the candidate antibody to the target O-GlcNAcylated myc peptide reacted with the O-GlcNAcylated target peptide, and did not cross-react with the unmodified target peptide (FIG. 2A, top row, "peptide 2-G"). It also did not cross-react with the GlcNAcylation site-specificity control, an O— GlcNAcylated p53 peptide (FIG. 2B, left panel). This indicates that the candidate antibody to the target O-GlcNAcylated c-myc peptide is a site-specific antibody to c-myc O-GlcNAcylated at Thr 48. Similarly, the candidate antibody to the unmodified myc peptide reacted with the unmodified target peptide (FIG. 2A, top row, "peptide 2N") and did not cross react with the O-GlcNAcylated target peptide. This indicates that the candidate antibody to the target unmodified c-myc peptide is a site-specific antibody to c-myc unmodified at Thr 48.

Also as disclosed in Example 2, candidate antibodies to the target O-GlcNAcylated p53 peptide were generated against a peptide in which Ser 149 was in GlcNAcylated form (e.g. peptide 1G). Candidate antibodies the unmodified p53 peptide were generated against a peptide in which Ser 149 was unmodified (e.g. peptide 1N).

Candidate site-specific antibodies to site-specific O-GlcNAcylated and unmodified myc proteins were characterized, using an O-GlcNAcylated p53 peptide, as the O-GlcNAcylated target peptide; the unmodified form of the same peptide, as the unmodified target peptide; an O-GlcNAcylated c-myc peptide as the GlcNAcylation site-specificity control peptide; and the unmodified form of the same c-myc peptide as the unmodified site-specificity control peptide.

It was found that the candidate antibody to the target O-GlcNAcylated p53 peptide reacted with the O-GlcNAcylated target peptide, and did not cross-react with the unmodified target peptide (FIG. 2A, bottom row, "Peptide 10"). It also did not cross-react with the GlcNAcylation site-specificity control, i.e the O-GlcNAcylated c-myc peptide (FIG. 2B, right panel). These results indicate that the candidate antibody to the target O-GlcNAcylated p53 peptide is a site-specific antibody for c-p53 O-GlcNAcylated at Ser 149. In a similar experiment, it was found that a candidate antibody to the unmodified p53 peptide is a site-specific antibody to p53 unmodified at Ser 149 (FIG. 2A, bottom row, "Peptide 1N").

Figure 3:
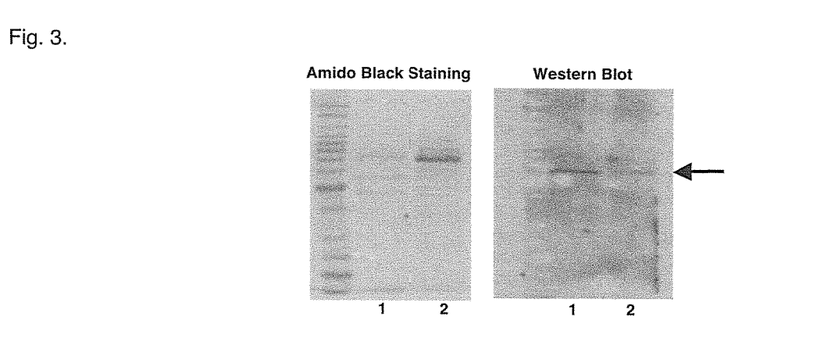
FIG. 3 shows Western blot analyses of O-GlcNAcylated c-myc localization; Western blot analysis (8-16% gel) was carried out with nuclear lysates (Lane 1) and cytosolic supernatants (Lane 2) obtained from MCF-7 cells using antibodies for O-GlcNAcylated c-myc (Peptide #2-G, 5,000-fold diluted); O-GlcNAcylated c-myc (68 kDa) is marked with an arrow; O-GlcNAcylated c-myc localization is primarily in the nucleus.

The antibodies characterized by the methods of the present invention also show their characteristic specificities when used to analyze protein GlcNAcylation in cell lysates. This specificity is seen, for example, the experiments of Example 3, wherein a site-specific antibody to the O-GlcNAcylated c-myc specifically detected this protein in nuclear and cytoplasmic lysates of normal breast and breast cancer cell lines (FIG. 3).

In summary, a method for of characterizing the protein O-GlcNAcylation site-specificity of a candidate antibody according to the present invention includes the steps of providing an O-GlcNAcylated target protein that is O-GlcNAcylated at a target O-GlcNAcylation site, or a peptide thereof that is O-GlcNAcylated at the target O-GlcNAcylation site; providing a corresponding unmodified target protein that is not O-GlcNAcylated at the target O-GlcNAcylation site, or a corresponding unmodified target peptide thereof; providing an O-GlcNAcylation site-specificity control protein that is O-GlcNAcylated at a non-target O-GlcNAcylation site, or a O-GlcNAcylation site-specificity control peptide thereof; providing a corresponding unmodified site-specificity control protein that is not O-GlcNAcylated at the non-target O-GlcNAcylation site, or an unmodified site-specificity control peptide thereof; providing a candidate site-specific antibody to the O-GlcNAcylated target protein; providing a candidate site-specific antibody to the unmodified target protein; reacting the candidate site-specific antibody to the O-GlcNAcylated target protein with the O-GlcNAcylated target protein or peptide; with the corresponding unmodified target protein or peptide; and with the O-GlcNAcylation site-specificity control protein or peptide; reacting the candidate site-specific antibody to the unmodified target protein; with the corresponding unmodified target protein or peptide; with the O-GlcNAcylated target protein or peptide; and with the corresponding unmodified site-specificity control protein or peptide; determining that the candidate site-specific antibody to the O-GlcNAcylated target peptide reacts specifically with the O-GlcNAcylated target protein or peptide, and does not cross-react with the corresponding unmodified target protein or peptide; and does not cross-react with the O-GlcNAcylation site-specificity control protein or peptide; characterizing the candidate antibody to the target O-GlcNAcylated peptide as a site-specific antibody to the O-GlcNAcylated target protein or peptide; determining that the candidate site-specific antibody to the unmodified target protein reacts specifically with the corresponding unmodified target protein or peptide, and does not cross-react with the O-GlcNAcylated target protein or peptide, or with the corresponding unmodified site-specificity control protein or the unmodified site-specificity control peptide; and characterizing the candidate site-specific antibody to the unmodified target protein or peptide as a site-specific antibody to the unmodified target protein or peptide.

The site-specific antibodies characterized by the method of the present invention have many uses in the detection and purification of GlcNAcylated proteins, in the screening of anti-cancer drugs, and in the diagnosis and treatment of cancer, as will be seen in the Examples.

The present invention also includes a method of detecting or quantitating the expression of a site-specific O-GlcNAcylated protein expressed in cells and biological samples, including the steps of obtaining a sample of cells, or of a biological material, performing an immunoassay of the sample with an antibody determined, by the previously described antibody characterization method, to be a site-specific antibody to the site-specific O-GlcNAcylated protein; and measuring in the sample the expression of the site-specific O-GlcNAcylated protein. Optionally, the expression of the corresponding unmodified protein can also be immunoassayed with an antibody determined, by the previously described antibody characterization method, to be a site-specific antibody for that protein. The immunoassay can be performed by any immunoassay technique known in the art, including but not limited to an ELISA assay, an immunoprecipitation assay, a chromatin immunoprecipitation assay, a Western Blot analysis, an immunofluorescence assay, or an immunohistochemical analysis.

This detection method of the present invention is useful for studying the effects of O-GlcNAcylation-altering treatments on cells or tissues, in applications ranging from basic research to the clinical monitoring of O-GlcNAcylation-altering treatments in animals or human patients. In the experiments of Example 4, for instance, it was determined, using antibodies of the present invention, that GlcNAcylated c-myc is primarily expressed in nuclear lysates of a normal mammary cell line and a mammary cancer cell line, and not in cytosolic lysates (FIG. 3).

The present invention also includes a method for diagnosing the presence of cancer in an animal, including the steps of obtaining a diagnostic sample of cells or tissues from an individual animal to be diagnosed for cancer; obtaining a control sample of corresponding control cells or control tissues from control animals; measuring the expression in the diagnostic and control samples of a site-specific O-GlcNAcylated protein by an immunoassay using an antibody characterized by the previously described characterization method as a site-specific antibody to the site-specific O-GlcNAcylated protein; comparing the expression of the site-specific O-GlcNAcylated protein in the diagnostic sample to the expression of the site-specific O-GlcNAcylated protein in the control samples; determining that the expression of the site-specific O-GlcNAcylated protein in the diagnostic sample is lower than the expression of the site-specific O-GlcNAcylated protein in the control samples; and diagnosing the presence of cancer in the individual animal to be diagnosed.

Figure 6:
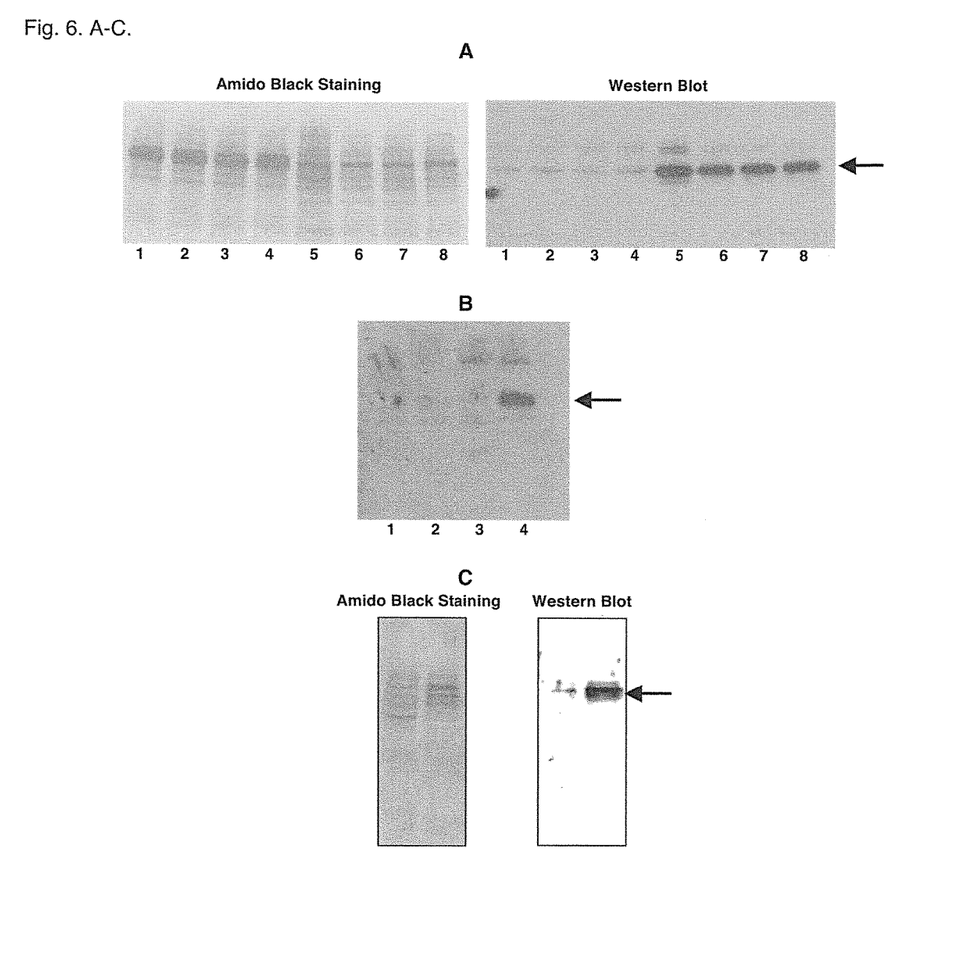

This method is illustrated in experiments disclosed in Example 5, FIG. 6A. It was found that the breast cancer cell line MCF-7 expresses much lower levels of O-GlcNAcylated c-myc than does the normal breast cell line MCF-10A. This difference was determined by in Western blots stained with a site-specific antibody to O-GlcNAcylated c-myc that had been characterized by the methods of the present invention (FIG. 6, right panel, compare lane 1, MCF-7 with control treatment vs lane 5, MCF-10A with control treatment). Similarly, in experiments disclosed in Example 7, it was found that MCF-7 expresses much lower levels of O-GlcNAcylated p53 than does MCF-10A (FIG. 7A, compare lane 1, MCF-7 cells with control treatment vs. lane 5, MCF-10 cells with control treatment). The findings could mean that the low levels of O-GlcNAcylated c-myc and p53 proteins in MCF-7 were induced by increased phosphorylated c-myc and p53 proteins, which can induce cancer cell proliferation and metastasis. It is also possible that low O-GlcNAcylation of these proteins permitted their hyperphosphorylation. In either case, the results indicate the utility of the antibodies of the present invention in detecting low O-GlcNAcylation as a biomarker of cancers whose pathology includes aberrant behavior of c-myc and/or p53, and possibly of other cancers.

The present invention also includes a method for screening a candidate drug for anti-cancer activity. In this method, candidate drugs are screened for ability to increase levels of cellular O-GlcNAcylated c-myc, and other GlcNAcylatable oncogenes or tumor suppressor genes, in tumor cells. Levels of O-GlcNAcylated proteins are determined by immunoassay with the site-specific antibodies characterized according to the previously described methods. A relationship between the ability of a drug to increase levels of O-GlcNAcylation of cellular oncogenes and its anti-cancer activity is shown experiments to be disclosed in Example 9.

A method for screening candidate drugs for anti-cancer activity according to the present invention includes the steps of: identifying a site-specific O-GlcNAcylated protein that is present at a lower level in cancer cells or tissues than in corresponding normal cells or tissues; treating an experimental sample of cancer cells or tissues with a candidate anti-cancer drug; treating a control sample of the same cancer cells or tissues with a control treatment; performing an immunoassay of the experimental and control samples with an antibody determined by the previously described antibody characterization method to be a site-specific antibody to the site-specific O-GlcNAcylated protein; measuring the expression of a site-specific O-GlcNAcylated protein in the experimental and control samples; determining that the level of the site-specific O-GlcNAcylated protein in the experimental sample is lower than in the control sample; and designating the candidate drug as having anti-cancer activity.

Once a candidate drug is found to increase levels of O-GlcNAcylation of cancer-associated proteins, its anti-cancer activity can be characterized in terms of antiproliferative activity, anti-metastatic activity, or both. The drug screening method according to the present invention therefore optionally includes the steps of determining the effect of the candidate drug upon cell proliferation, including the steps of treating an experimental sample of cancer cells with the candidate drug; treating a control sample of the same cancer cells with a control treatment; measuring cell proliferation in the experimental and control samples; comparing the cell proliferation of the experimental sample to that of the control sample; determining that cell proliferation is lower in the experimental sample than in the control sample; and designating the candidate drug as having anti-proliferative activity. The drug screening method according to the present invention also optionally includes the steps of determining the effect of the candidate drug upon cellular invasion, including the steps of treating an experimental sample of cancer cells the candidate drug; treating a control sample of the same cancer cells with a control treatment; measuring cellular invasiveness in the experimental and control samples; comparing the cellular invasiveness of the experimental sample to that of the control sample; determining that cellular invasiveness is lower in the experimental sample than in the control sample; and designating the candidate drug as having anti-invasive activity.

The drug screening method of the present invention is superior to prior art screening methods, such as those which detect inhibitors of GlcNAcase in artificial contexts. An example of the prior art is the technique of measuring the cleavage of a fluorescent pseudosubstrate of GlcNAcase, 4-methylumbelliferol (4-MU)-GlcNAc (7). Inhibitors found to be effective at inhibiting this cleavage were found not to be useful for increasing levels of O-GlcNAcylation of particular cancer related proteins, probably because of the target-sequence dependent activity of O-GlcNAcase.

Figure 5:
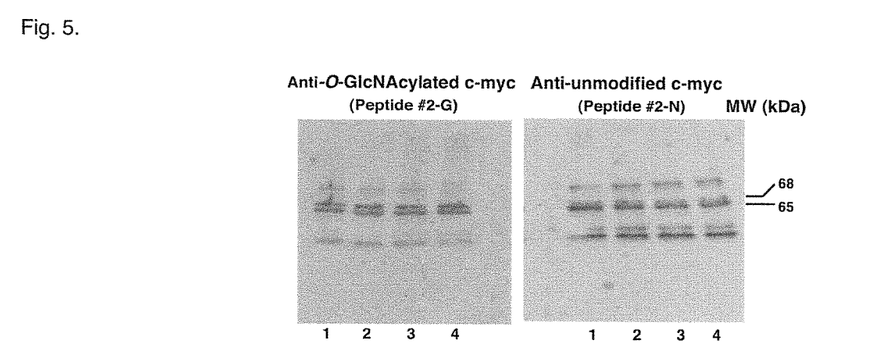
FIG. 5 shows Western blots showing O-GlcNAcylated c-myc levels after treatment of MCF-7 cells for 24 hr with 1% DMSO (Lane 1), 2 mM O-GlcNAcase inhibitor, streptozotocin (STZ) (Lane 2) and N6-methyladenosine 5'-monophosphate (Lane 3), and media (control) (Lane 4); Western blot analysis was carried out with nuclear lysates (20 µg/lane) using antibodies for O-GlcNAcylated c-myc (Peptide #1-G, 5,000-fold diluted); the inhibitors were dissolved in DMSO (final concentration in media, 1%)

For example, prior art methods indicated that the compounds streptozoticin (STZ), methyladenosine 5'-monophosphate and acetazolamide have GlcNAcase activity. In experiments disclosed in Examples 5 and 7, it was found that N6-methyladenosine 5'-monophosphate and acetazolamide did not increase the levels of O-GlcNAcylated c-myc in MCF-7 cells (FIGS. 5 and 6A). Interestingly, N6-methyladenosine 5'-monophosphate and acetazolamide did increase levels of O-GlcNAcylated p53 in MCF-7 cells (FIG. 7B). The site-specific protein O-GlcNAcylation antibodies of the present invention make it possible to screen potential anti-cancer compounds in the context of actual cancer-associated proteins in cancer cell environments.

Figure 8:
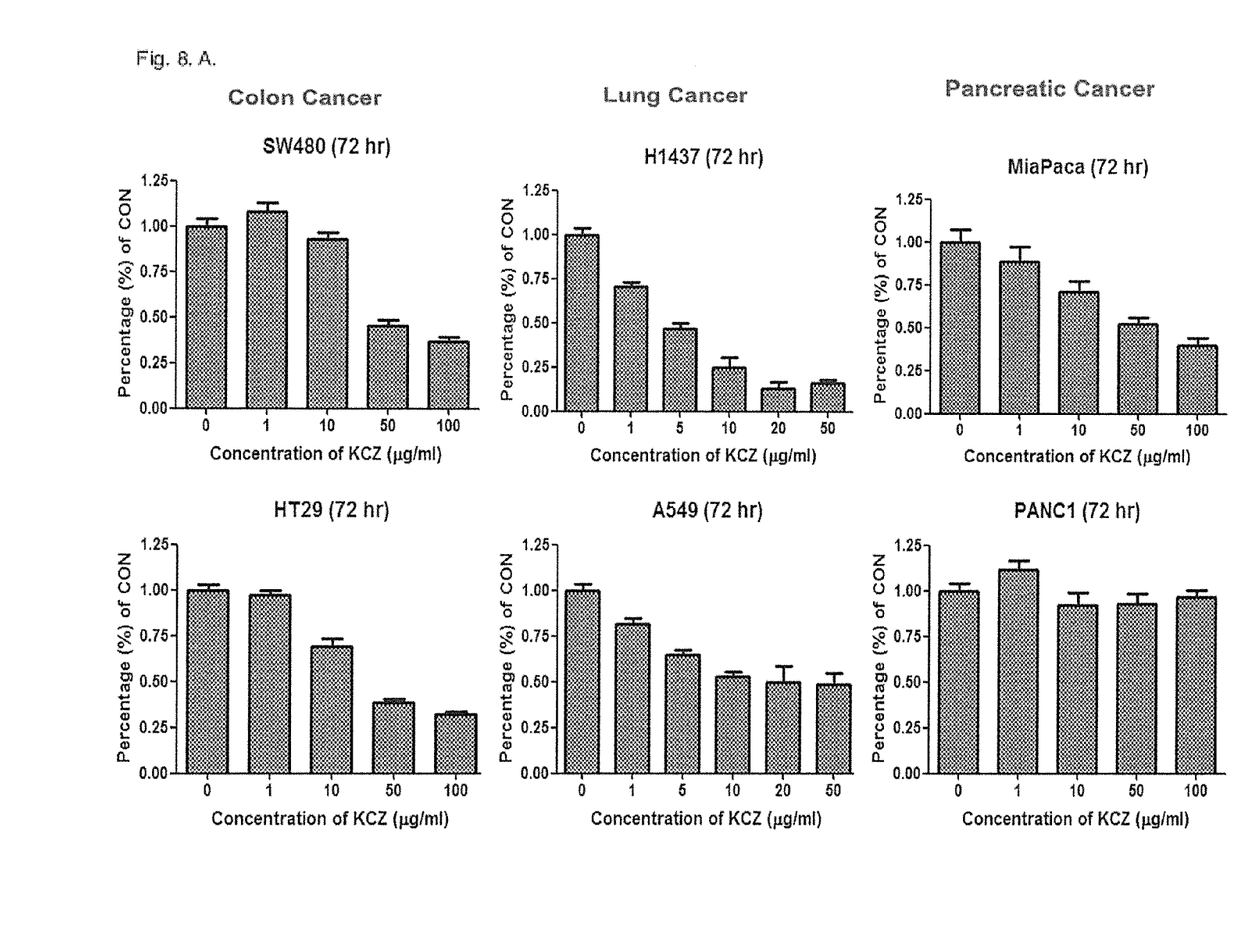
FIG. 8A: cell proliferation assays after seeding 3,000-5,000 cells in a 96-well plate with and without treatment with 1, 5, 10, 20, 50 or 100 µM ketoconazole (KCZ) dissolved in DMSO (final concentration, 1%) for 72 hr; the cell number was counted after staining the cells with 3-(4,5-dimethylthiazol-2-yl)2,5-diphenyl-tetrazolium bromide (MTT); the ketoconazole treatment inhibited cell proliferation of colon cancer cells, SW480 and HT29, by 63.3% and 67.4%, respectively, of lung cancer cells, H1437 and A549, by 44.9% and 51.3%, respectively, and of a pancreatic cancer cell, Mia Paca-2, by 60.2%, in a dose-dependent manner; whereas the same treatments failed to inhibit PANC1 cell proliferation.
FIG. 8B: cell invasion assays with colon cancer cells, SW480 and HT29 cells, and breast cancer cells, MCF-10CA1A, after seeding 3,000-5,000 cells in a 24 trans-well plate using the QCM ECMatrix cell invasion assay kit (EMD Millipore) with and without treatment of 100 µM ketoconazole dissolved in DMSO (final concentration, 1%) for 72 hr; the ketoconazole treatment inhibited 100% of migration of colon cancer cells and partially inhibited migration of the breast cancer cells.

The present invention also includes a method of treating cancer in an animal host, including the steps of administering an effective amount of a compound which increases the level of O-GlcNAcylated c-myc in cancer cells; increasing the level of O-GlcNAcylated c-myc in cancer cells in the host; and treating cancer in the animal host. Preferred compounds are of the imidazole class, especially ketoconazole. Ketoconazole was selected as an anti-cancer compound on the basis of its ability to increase levels of O-GlcNAcylated c-myc in cancer cells. In experiments disclosed in Example 9, cell proliferation assays were carried out with and without treatment of 0-50 μM ketoconazole for 72 hr (Example 9, FIG. 8, Panel A). The ketoconazole treatment (50 μM for 72 hr) inhibited proliferation of colon cancer cells, SW480 and HT29, by 63.3% and 67.4%, respectively, of lung cancer cells, H1437 and A549, by 44.9% and 51.3%, respectively, and of a pancreatic cancer cell line, Mia Paca-2, by 60.2%, in a dose-dependent manner. These results demonstrated that treatment of ketoconazole, which increases levels of O-GlcNAcylated c-myc, inhibited the proliferation of MCF-7 breast cancer cells as well as colon, lung and pancreatic cancer cells.

Ketoconazole also proved to decrease invasion of cancer cells in an extracellular matrix invasion assay which strongly predicts decreased invasion and metastasis in vivo. Ketoconazole treatment resulted in a loss of cell invasiveness of the two colon cancer cell types, and a slight loss of cell invasiveness of breast cancer cells (FIG. 8, Panel B). Ketoconazole also decreased the migration of colon cancer cells and a subset of pancreatic cancer cells in a wound healing assay (Table 1). It is possible that the ketoconazole and other agents that increase the GlcNAcylation of c-myc or p53 produce their anti-cancer effects by reducing the phosphorylation of the same or nearby critical sites in the c-myc molecules. Since treatments which increase cellular levels of O-GlcNAcylated c-myc in cancer cells produce anticancer effects, including antiproliferative and antimetastatic effects, it is expected that treatments that increase levels of O-GlcNAcylated p53 will also have anticancer effects. It is also expected that treatments that increase levels of both O-GlcNAcylated c-myc and O-GlcNAcylated p53 will also have anticancer effects, possibly greater effects than either treatment alone. As previously stated, the compounds N6-methyladenosine 5'-monophosphate and acetazolamide increase levels of O-GlcNAcylated p53 (FIG. 7B) but not O-GlcNAcylated c-myc (FIGS. 5 and 6A) in MCF-7 cells (FIG. 7B).

Based on these findings, the present invention includes a method for treating cancer in an animal host, including the steps of administering to an animal host an effective amount of a compound that increases the level of O-GlcNAcylated p53 in cancer cells; increasing the level of O-GlcNAcylated p53 in cancer cells in the host; and treating cancer in the animal host. A preferred compound is N6-methyladenosine 5'-monophosphate. The present invention also includes a combination therapy method of treating cancer in an animal host, including the steps of administering an effective amount of at least one compound that increases the level of O-GlcNAcylated c-myc in cancer cells, and at least one compound that increases the level of O-GlcNAcylated p53 in cancer cells, increasing the level of O-GlcNAcylated c-myc and O-GlcNAcylated p53 in cancer cells in cancer cells in the host; and treating cancer in the animal host. The preferred combination of compounds is ketoconazole and N6-methyladenosine 5'-monophosphate.

Interestingly, some pancreatic cancer cell lines proved to be susceptible to the antiproliferative and anti-metastatic effects of ketoconazole, and some lines are resistant. For example, the pancreatic cancer cell line Mia Paca-2 showed reduced migration in a wound healing assay, and reduced proliferation after ketoconazole treatment (Table 1, FIG. 8, Panel A). In contrast, cells of the pancreatic cancer cell line PANC-1 show no significant differences in migration or proliferation after ketoconazole treatment (Table 1, FIG. 8, Panel A).

On the basis of these findings, the present invention includes a method of distinguishing subclasses of pancreatic cancer according to the sensitivity of pancreatic cancer cells to an imidazole derivative, including the steps of treating an experimental sample of pancreatic cancer cells with an imidazole derivative, treating a control sample of the pancreatic cancer cells with a control treatment, measuring a property of the pancreatic cancer cells in the experimental and control samples, determining whether the property was affected by treatment with the imidazole derivative, determining that the pancreatic cancer cells are of an imidazole-derivative sensitive subclass if the property is affected by treatment with the imidazole derivative; and determining that the pancreatic cancer cells are of an imidazole-derivative insensitive subclass if the property is not affected by treatment with the imidazole derivative. The properties tested include, but are not limited to, cell proliferation, cell invasiveness, a level of the site-specific O-GlcNAcylated c-myc, a level of site-specific O-GlcNAcylated p53, or a combination of the levels.

The present invention also includes a method of personalized pancreatic cancer therapy in an animal host, based on the imidazole sensitivity subclass distinction. The method includes the steps of obtaining a sample of pancreatic cancer cells of the animal host, determining whether the pancreatic cancer is of the imidazole-derivative sensitive subclass, according the previously described method of distinguishing sublclasses, and treating the animal host with an imidazole derivative only if the pancreatic cancer is of the imidazole-derivative sensitive subclass.

Most of the techniques used to produce antibodies in the present disclosure are widely practiced in the art, and most practitioners are familiar with the standard resource materials, which describe specific conditions and procedures. However, for convenience, the following paragraph may serve as a guideline.

Antibody production: Antibodies (immunoglobulins) may be either monoclonal or polyclonal and are raised against the immunogen. Such immunogens can be used to produce antibodies by standard antibody production technology well known to those skilled in the art as described generally in Harlow and Lane, Antibodies: A laboratory Manual, Cold Spring Harbor Laboratory, Cold Spring Harbor, N.Y., 1988 and Borrebaeck, Antibody Engineering—A Practical Guide, W. H. Freeman and Co., 1992. Antibody fragments may also be prepared from the antibodies and include Fab, F(ab')2, and Fv by methods known to those skilled in the art. For producing recombinant antibody, messenger RNAs from antibody producing B-lymphocytes of animals, or hybridoma are reverse-transcribed to obtain complementary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. The methods used with and the utility of the present invention can be shown by the following non-limiting examples and accompanying figures.

EXAMPLES

Materials and Methods

Materials.

Pan-specific O-GlcNAc antibodies were obtained from Abcam. Nα-Fmoc serine (Ser) and threonine (Thr) were from Sussex Research (Ottawa, Canada). Protein-G affinity resin and Reacti® Gel were from Pierce and SulfaLink® coupling resin was from Thermo Scientific. Molecular weight standards (BenchMark™ Protein Ladder) were from Invitrogen. Minimal essential medium with Earle's (MEM/EBSS) and Dulbecco's modified eagle medium: nutrient mixture F-12 (DMEM/F12) media were obtained from Hyclone (Logan, Utah). The QCM ECMatrix cell invasion assay kit was from EMD Millipore. O-GlcNAcylation and unmodified site-site-specific c-myc and p53 antibodies and BSA conjugated with O-GlcNAcylated c-myc and p53 peptides are from Detroit R&D. Other reagents were obtained from Sigma Chemical Co. (St. Louis, Mo.).

Methods.

Conventional ELISA for Titer Measurements:

Direct ELISA was carried out using BSA and peptide conjugated to BSA. Briefly, 1 μg of free BSA and peptide-conjugated BSA were coated on a 96-well plate overnight in 1 M sodium bicarbonate, pH 9.6. Non-specific sites were blocked by the addition of 0.2 ml of 10% nonfat dry milk in TBS, pH 7.5, and plates were incubated for 2 hr at room temperature. Anti-serum was diluted 50,000- to 1,000,000-fold in TBS and added to wells and incubated for 2 hr at room temperature, followed by incubation for 1 hr with various dilutions of goat anti-rabbit IgG-horseradish peroxidase (HRP) secondary antibody. After washing, the color was developed by the addition of 0.2 ml of TMB (3,3',5,5'-tetramethylbenzidine). The reaction was stopped in ~30 min by addition of 50 μl of 2 $NH_2SO_4$, and the absorbance at 450 nm was obtained using a microtiter plate reader.

MCF-7 (Breast Tumor) and MCF10A (Normal) Cell Culture:

MCF-7 cells were grown in MEM/EBSS media (Hyclone, Logan, Utah) supplemented with 10% fetal bovine serum and 0.01 mg/mL insulin. MCF-10A cells were grown in DMEM/F12 media (Hyclone) supplemented with 5% horse serum, 0.5 mg/mL hydrocortisone, 10 mg/mL insulin, 20 ng/mL EGF, 0.1 mg/mL cholera endotoxin, 100 units/mL penicillin-streptomycin and 2 mM glutamine. The glucose concentration of MEM/EBSS and DMEM/F12 media are 6 mM and 18 mM, respectively. Cells were maintained in humidified atmosphere with 95% air and 5% CO2 at 37° C.

Example 1

Characterization of Sensitivity of Site-Specific Anti-Peptide Antibodies for O-GlcNAcylated and Corresponding Unmodified p53 and c-Myc Proteins Antibody titers were measured with 5,000- through 1,000,000-fold diluted immune sera using ELISA plates coated with free BSA and O-GlcNAcylated and unmodified c-myc or p53 peptides conjugated to BSA (1 μg/well).

Figure 1:
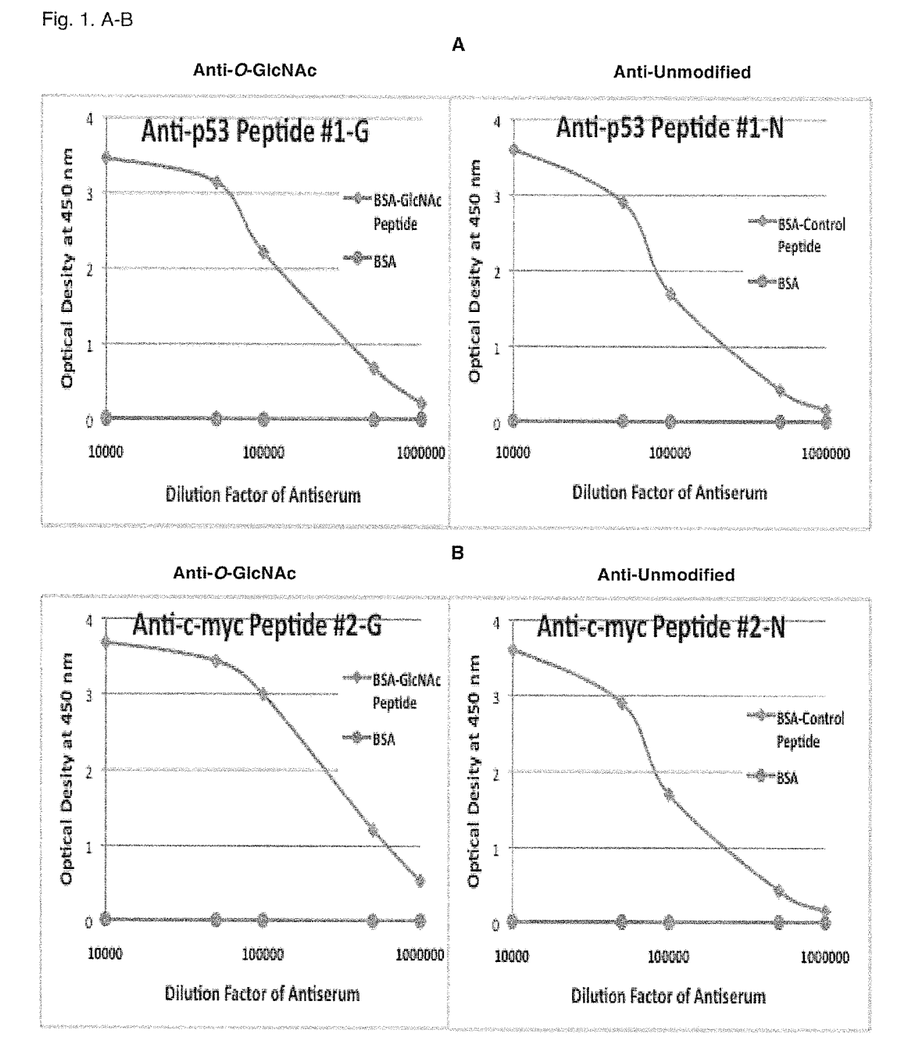
FIGS. 1A and 1B are graphs showing titers (dilution factor at 50% of maximum OD, sensitivity) of anti-sera for O-GlcNAcylated and corresponding unmodified p53 (Panel A) and c-myc (Panel B) proteins; Panel A shows titer measurements of anti-sera for Ser-149 O-GlcNAcylated and unmodified p53 by ELISA using a plate coated with BSA conjugated p53 peptides; Panel B shows titer measurements of anti-sera for Thr-58 O-GlcNAcylated and unmodified c-myc by ELISA using a plate coated with BSA conjugated c-myc peptides; optical density (OD) at 450 nm obtained with BSA was subtracted from the OD of BSA-peptide conjugates for each titer calculation.

Whereas anti-sera for Ser-149 O-GlcNAcylated (Peptide #1-G) and unmodified (Peptide #1-N) p53 showed almost no cross-reactivity (optical density at 450 nm: 0) with BSA, the immune sera showed very high cross-reactivity (optical density at 450 nm: 3.4 and 3.6, respectively, with 10,000-fold dilution) (FIG. 1, Panel A). Titers (dilution factor at 50% of maximum OD) of the p53 anti-sera were 135,000 and 98,000, respectively.

Whereas anti-sera for Thr-48 O-GlcNAcylated (Peptide #2-O) and unmodified (Peptide #2-N) c-myc showed almost no cross-reactivity (optical density at 450 nm: 0) with BSA, the immune sera showed very high cross-reactivity (optical density at 450 nm: 3.7 and 3.6, respectively, with 10,000-fold dilution) (FIG. 1, Panel B). Titers (dilution factor at 50% of maximum OD) of the p53 anti-sera were 270,000 and 99,000, respectively.

The results showed that anti-sera for both O-GlcNAcylated and unmodified p53 and c-myc are extremely sensitive. The O-GlcNAc moiety of the Ser or Thr induces higher sensitivity and O-GlcNAcylated Thr is a better immunogen than O-GlcNAcylated Ser.

Example 2

Characterization of Specificity of Site-Specific Antibodies for O-GlcNAcylated and Corresponding Unmodified p53 and c-Myc Proteins To determine the specificity of the antibodies for O-GlcNAcylated and corresponding unmodified p53 and c-myc proteins, Western blot analysis was carried out with BSA (2 μg/lane) and O-GlcNAcylated and unmodified p53 and c-myc antigen peptides conjugated to BSA (0.2 μg/lane, 10 times less than the BSA, a negative control).

Specificity of the antibodies was determined by Western blot analysis with BSA conjugated with O-GlcNAcylated and unmodified c-myc and p53 peptides (FIG. 2A). BSA negative controls were produced by simultaneously carrying out conjugations with the EDC or sulfo-SMCC methods but without addition of peptides. Western blot analyses of BSA and BSA conjugated with O-GlcNAcylated and corresponding unmodified c-myc peptides (Peptide #2-0 and #2-N) were carried out using c-myc antibodies. c-Myc antibodies for the O-GlcNAcylated peptides did not cross-react with unmodified peptides and c-myc antibodies for the unmodified peptide did not cross-react with the O-GlcNAcylated peptides (FIG. 2A, Top middle). c-Myc antibodies for O-GlcNAcylated and unmodified peptides (Peptide #1-G and Peptide #1-N) were form-specific and O-GlcNAcylated peptides minimally cross-reacted with the unmodified peptides (Peptide #4-G) (FIG. 2A, Top left and right, respectively). However, the c-myc antibodies for unmodified peptides (Peptide #4-N) were not form-specific (data not shown). Antibodies for the O-GlcNAcylated (Peptide #1-G) p53 peptides primarily cross-reacted with the BSA conjugated with O-GlcNAcylated peptides, with minimal cross-reactivity with unmodified peptides (FIG. 2A, Bottom). This result confirmed specificity of the antibodies. The BSA-Peptides showed monomer, dimer and even higher polymers because, during peptide conjugation, various peptide-conjugated BSA polymers were produced by cross-linking chemicals.

Example 3

Evidence that the Anti-Peptide Antibodies are O-GlcNAcylation Site-Specific for Ser-149 of p53 and Thr-58 of c-Myc Proteins Specificity of the antibodies for O-GlcNAcylated p53 and c-myc proteins was further determined using O-GlcNAcylated p53 and c-myc antigen peptides. Western blot analysis was carried out with BSA (2 μg/lane) and O-GlcNAcylated p53 (Peptide #1-G) and c-myc (Peptide #2-0) antigen peptides conjugated to BSA (0.2 μg/lane, 10 times less than the BSA, a negative control) with antibodies for O-GlcNAcylated p53 and c-myc proteins (FIG. 2B).

Thr-58 O-GlcNAcylation site-specific c-myc antibodies did not cross-react with O-GlcNAcylated p53 peptides, and Ser-149 O-GlcNAcylation site-specific p53 antibodies did not cross-react with O-GlcNAcylated c-myc peptides (FIG. 2B). This result demonstrated that the O-GlcNAcylation site-specific c-myc and p53 antibodies recognize specifically the Thr-58 and Ser-149 O-GlcNAcylation sites of c-myc and p53, respectively, which are NOT pan-O-GlcNAcylation antibodies. Pan-O-GlcNAcylation antibodies recognize only the O-GlcNAc moiety of amino acid, which are not useful to determine Thr-58 and Ser-149 O-GlcNAcylation sites of c-myc and p53, respectively.

Example 4

O-GlcNAcylated c-Myc is Expressed Primarily in Nucleus

For c-myc Western blot analysis, nuclear lysates isolated from MCF-7 and MCF10A cells were used because high levels of c-myc proteins were detected in nuclear lysates but NOT in cytosol-containing supernatant (FIG. 3). Use of nuclear lysates, which express high levels of c-myc proteins, increased the sensitivity of the Western blot analysis.

Figure 4:
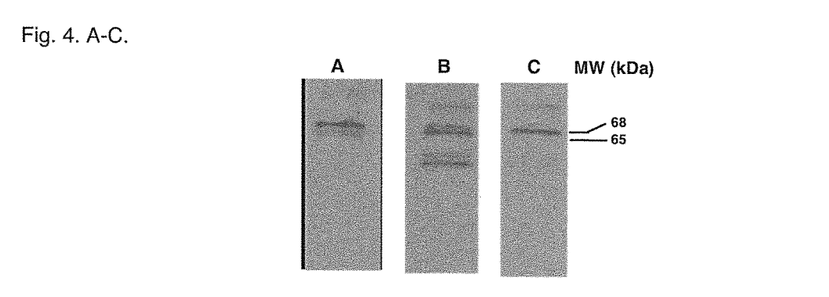
FIGS. 4A-4C show Western blots of O-GlcNAcylated (Panel A), unmodified (Panel B) and phosphorylated (Panel C) c-myc proteins in nuclear lysates immunoprecipitated with monoclonal antibodies (C33, Santa Cruz) and detected by Western blot analysis (8-16% gel) using c-myc antibodies for O-GlcNAcylated (Peptide #2-G, 5,000-fold diluted), unmodified (Peptide #2-N, 5,000-fold diluted) and phosphorylated (Santa Cruz, 1,000-fold diluted) c-myc antibodies; molecular weights of the c-myc proteins were estimated using MW standards (BenchMark™ Protein Ladder, Invitrogen)

Immunoprecipitation of c-myc proteins expressed in MCF-7 cell nuclear lysates was carried out using monoclonal c-myc antibodies (C-33, pan-c-myc antibody, Santa Cruz). A 68 kDa band was identified as Thr-58 O-GlcNAcylated c-myc (FIG. 4A) and a 65 kDa band was identified as unmodified c-myc (FIG. 4B) by Western blot analysis using O-GlcNAcylation site-specific and corresponding unmodified c-myc antibodies. A 68 kDa protein was recognized by antibodies for phosphorylated c-myc (pThr-58/pSer62, Santa Cruz) (FIG. 4C). This result verified that O-GlcNAcylated c-myc (68 kDa) migrated slower than unmodified c-myc (65 kDa). No other proteins with and without O-GlcNAcylation expressed in MCF-7 cells cross-reacted except for the O-GlcNAcylated c-myc proteins with the antibodies proving that the antibodies are Thr-58 O-GlcNAcylation site-specific.

Example 5

Dramatically Increased O-GlcNAcylated c-Myc Levels after an O-GlcNAcase Inhibitor, Ketoconazole Treatment (Anti-Breast Cancer Drug Candidate)

MCF-7 breast cancer cells were treated for 24 hr with 1% DMSO, with an O-GlcNAcase inhibitor, streptozotocin (STZ), with N6-methyladenosine 5'-monophosphate (an O-GlcNAcase inhibitor discovered through by screening with the pseudofluorescent substrate 4-methylumbelliferol (4-MU)-GlcNAc (7)) or with media (control) (FIG. 5). Western blot analysis revealed that the O-GlcNAcase inhibitors, STZ and N6-methyladenosine 5'-monophosphate, failed to increase O-GlcNAcylated c-myc levels in MCF-7.

O-GlcNAcase inhibitors, which increased O-GlcNAcylation levels of proteins by preventing cleavage of an O-GlcNAc moiety of Ser or Thr residues, were identified using the antibodies of the present invention. MCF-7 breast cancer cells (FIG. 6. Panel A, Lanes 1-4) and MCF10A normal breast cells (FIG. 6. Panel A, Lanes 5-8) were treated for 4 hr with 1% DMSO (FIG. 6, Panel A, Lanes 1 and 5), the O-GlcNAcase inhibitors acetazolamide (FIG. 6, Panel A, Lanes 2 and 6) and N6-methyladenosine 5'-monophosphate (FIG. 6, Panel A, Lanes 4 and 7) or media (control) (FIG. 6, Panel A, Lanes 4 and 8). Western blot analysis (8-16% gel) was carried out with cell lysates (20 µg/lane) using antibodies for O-GlcNAcylated c-myc (Peptide #1-G, 5,000-fold diluted). The O-GlcNAcase inhibitors acetazolamide (FIG. 6, Panel A, Lanes 2 and 6) and N6-methyladenosine 5'-monophosphate failed to increase O-GlcNAcylated c-myc levels in either MCF-7 or MCF10A cells.

MCF-7 cells were treated for 4 hr with 1% DMSO (negative control) or 2 mM buspirone or ketoconazole in DMSO to verify increased O-GlcNAcylated c-myc levels after 2 mM ketoconazole treatment. Western blot analysis was carried out with 10% gel electrophoresis using nuclear lysates obtained from MCF-7 cells with antibodies for O-GlcNAcylated c-myc (Peptide #2-O). Whereas the O-GlcNAcylated c-myc level did not increase after buspirone treatment, the level dramatically increased after ketoconazole treatment (FIG. 6, Panel B). There was no increase in unmodified c-myc protein after ketoconazole treatment as verified with antibodies for unmodified c-myc (Peptide #2-N) by Western blot analysis.

MCF-7 cells were treated for 4 hr with 1% DMSO (negative control) or 2 mM ketoconazole in DMSO and an O-GlcNAcylated c-myc band was detected using a second antibody for O-GlcNAcylated c-myc (Peptide #1-G). The O-GlcNAcylated c-myc level dramatically increased after ketoconazole treatment as detected with the antibodies (FIG. 6, Panel C).

Example 6

Lactate Dehydrogenase (LDH) Cytotoxicity Assay of Ketoconazole Treated MCF-7 and MCF10A Cells Increased O-GlcNAcylated c-myc levels in MCF-7 cells induced cell death. MCF-7 tumor cell death after 2 mM ketoconazole treatment was compared with MCF10A normal cell death by LDH cytotoxicity assay. After treatment of cells for 4 hr, extracellular media and Triton X-100 solubilized cells were obtained and oxidation of NADH to NAD+ in both fractions was monitored for 2 min at a 340 nm to obtain total (media+cells) LDH release. The ketoconazole treatment increased cell death in MCF-7 cells 84% higher than in MCF10A cells as determined by LDH cytotoxicity assays.

The results demonstrated that ketoconazole treatment increased Thr-58-O-GlcNAcylated c-myc level and induced cell death in MCF-7 cells.

Example 7

Increased O-GlcNAcylated p53 Levels after an O-GlcNAcase Inhibitor, Acetazolamide or N6-Methyladenosine 5'-Monophosphate Treatment (Anti-Breast Cancer Drug Candidates)

Figure 7:
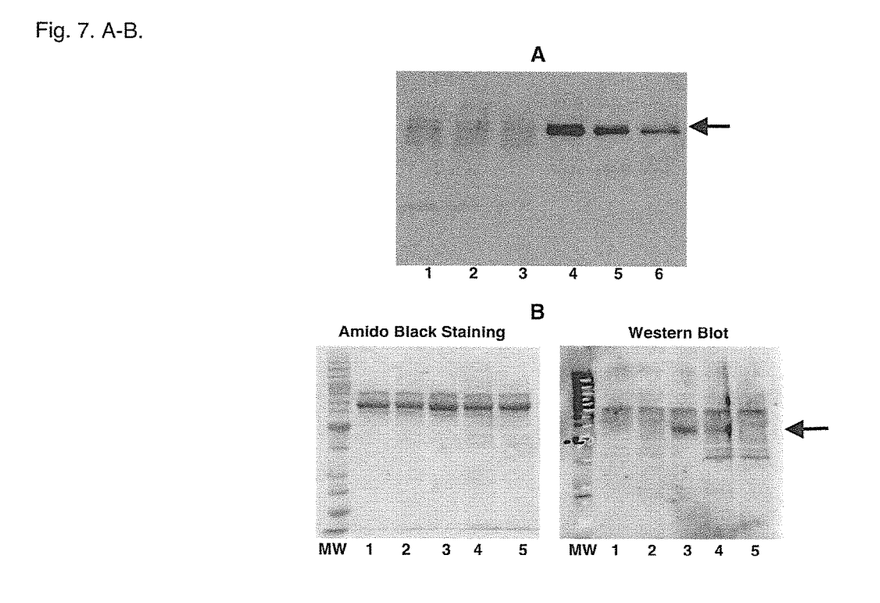
FIG. 7A shows p53 levels in in MCF-7 (Lanes 1 through 3) and MCF10A (Lanes 4 through 6) cells after treatment of the cells for 4 hr with media (control) (Lanes 1 and 4), 1% DMSO (Lanes 2 and 5) and an O-GlcNAcase inhibitor, buspirone (Lanes 3 and 6); Western blot analysis (8-16% gel) was carried out with cell lysates (20 µg/lane) using antibodies for O-GlcNAcylated p53 (Peptide #1-G, 10-mer, 5,000-fold diluted)
FIG. 7B shows, increased O-GlcNAcylated p53 levels after treatment of MCF-7 cells for 24 hr with O-GlcNAcase inhibitors, acetazolamide (Lane 3) and N6-methyladenosine 5'-monophosphate (Lane 4); Western blot analysis was carried out with cytosol-containing supernatant (40 µg/lane) using antibodies for O-GlcNAcylated p53 (Peptide #1-G, 5,000-fold diluted); STZ was dissolved in DMSO (final concentration in media, 1%); Lane 1, 1% DMSO, Lane 2, streptozotocin (STZ), Lane 3, acetazolamide, Lane 4, N6-methyladenosine 5'-monophosphate and Lane 5, media (control); O-GlcNAcylatylated p53 is marked with an arrow.

When MCF-7 and MCF10A cells were treated for 4 hr with and without treatment of 1% DMSO (negative control) or 0.5 mM buspirone in DMSO, buspirone treatment failed to increase O-GlcNAcylated p53 expression in MCF-7 and MCF10A cell lysates (FIG. 7, Panel A).

MCF-7 cells were grown for 24 hr with treatment of 1% DMSO (negative control) or 2 mM STZ or acetazolamide dissolved in DMSO or 2 mM N6-methyladenosine 5'-monophosphate dissolved in media. The cells were harvested and cytosol-containing supernatants were obtained.

Levels of O-GlcNAcylated and unmodified p53 proteins in cytosol-containing supernatants were detected using antibodies for O-GlcNAcylated p53 (Peptide #1-G) and unmodified p53 (Peptide #1-N), respectively, by Western blot analysis. Levels of O-GlcNAcylated p53 increased after acetazolamide or N6-methyladenosine 5'-monophosphate treatment (FIG. 7, Panel B). Acetazolamide was a potent inducer of O-GlcNAcylated p53 (FIG. 7, Panel B) but it did not increase O-GlcNAcylated c-myc levels in nucleus (data not shown).

Example 8

Extremely Low Expression of Thr-58 O-GlcNAcylated c-Myc and Ser-149 O-GlcNAcylated p53 Proteins in MCF-7 Breast Cancer Cells Compared with in MCF10A Normal Breast Cells Expression of both O-GlcNAcylated c-myc and p53 proteins in MCF-7 cells were extremely low compared with the levels in MCF10A cells (FIG. 6, Panel A and FIG. 7, Panel A, respectively), which suggested that the low levels of O-GlcNAcylated c-myc and p53 proteins in MCF-7 were induced by increased phosphorylated c-myc and p53 proteins, which is involved with cancer cell proliferation and metastasis. The lower O-GlcNAcylated c-myc and p53 protein levels detected in MCF-7 cells increased after treatment of ketoconazole (FIG. 6) and acetazolamide or N6-methyladenosine 5'-monophosphate (FIG. 7), respectively.

Example 9

Inhibition of Cancer Cell Proliferation and Invasion by Treatment of an O-GlcNAcase Inhibitor Ketoconazole (KCZ)(Anti-Breast Cancer Drug Candidate O-GlcNAcylated c-myc and p53 expression levels in MCF-7 cells were much lower than the expression in normal breast cells, MCF10A (FIG. 6, Panel A and FIG. 7, Panel A, respectively), which strongly suggested that decreased O-GlcNAcylated c-myc or p53 expression levels most likely induces cancer cell proliferation and invasiveness. Thus, increased O-GlcNAcylated c-myc or p53 expression levels after treatment with O-GlcNAcase inhibitors inhibit cancer cell proliferation and migration. Indeed, treatment of MCF-7 cells with 2 mM ketoconazole, an O-GlcNAcase inhibitor, for 4, hr dramatically increased O-GlcNAcylated c-myc levels (FIG. 6, Panels B and C) and increased cell death in MCF-7 cells 84% higher than in MCF10A non-cancerous cells as evidenced by lactate dehydrogenase (LDH) cytotoxicity assays. Cell proliferation assays were carried out after seeding 3,000-5,000 cells in a 96-well plate with and without treatment of 50 μM ketoconazole dissolved in DMSO (final concentration, 1%) for 72 hr (FIG. 8, Panel A). The cell number was counted after staining the cells with 3-(4,5-dimethylthiazol-2-yl)2,5-diphenyl-tetrazolium bromide (MTT). The ketoconazole treatment (50 μM for 72 hr) inhibited cell proliferation of colon cancer cells, SW480 and HT29, by 63.3% and 67.4%, respectively, lung cancer cells, H1437 and A549, by 44.9% and 51.3%, respectively, and a pancreatic cancer cell, Mia Paca-2, by 60.2% in a dose-dependent manner (0 through 50 μM) (FIG. 8, Panel A).

These results demonstrated that treatment of ketoconazole inhibited the proliferation of MCF-7 breast cancer cells as well as colon, lung and pancreatic cancer cells.

Wound healing assays were also carried out to verify inhibition of cell migration after ketoconazole treatment. Whereas 55.3% of Mia Paca-2 cells migrated toward a scratched field after 24-hr treatment, only 11.6% of the cells migrated after treatment with 100 μM ketoconazole (Table 1). PANC-1 cells, which failed to increase Thr-58-O-GlcNAcylated c-myc expression and cell proliferation after ketoconazole treatment, showed no significant difference of cell migration after 24 hr with 100 μM ketoconazole treatment.

Cell invasiveness of SW480 and HT29 human colon adenocarcinoma cells and MCF10CA1A breast cancer cells with and without 72 hr treatment with 100 μM ketoconazole was studied in 24-well plates using the QCM ECMatrix cell invasion assay kit (EMD Millipore). Ketoconazole treatment resulted in a loss of cell invasiveness of the two colon cancer cell types and a slight loss of cell invasiveness of the breast cancer cells (FIG. 8, Panel B).

Cell proliferation (FIG. 8, Panel A) and cell migration (FIG. 8, Panel B) of colon cancer cells, SW480 and HT29, were inhibited after 100 μM ketoconazole treatment.

The results demonstrated that treatment with ketoconazole, an O-GlcNAcase inhibitor, increased the level of Thr-58-O-GlcNAcylated c-myc and inhibited cell proliferation in MCF-7, SW480, HT29, H1437, A549 and Mia Paca-2 cells, and decreased invasiveness and migration of breast, colon, lung and pancreatic cancer cells.

TABLE 1

Wound healing assays to measure inhibition of cell migration toward scratched area with and without treatment of 100 μM ketoconazole dissolved in DMSO (final concentration, 1%). Percent of cells migrated toward a scratched field are shown. The ketoconazole treatment inhibited cell migration of a pancreatic cancer cell, Mia Paca-2, by 78% [(36/46 × 100) and (43/55 × 100) in 24 and 48 hr, respectively] whereas failed to inhibit PANC1 cell migration. The ketoconazole treatment slightly inhibited cell migration of colon cancer cells, SW480 and HT29 in 24 hours.

| Pancreatic Cancer (% cells migrated) | | | | |
|---|---|---|---|---|
| | Mia Paca-2 | | PANC1 | |
| Time (hr) | Control (1% DMSO) | Ketoconazole | Control (1% DMSO) | Ketoconazole |
| 0 | 0 | 0 | 0 | 0 |
| 24 | 46 | 10 | 6 | 6 |
| 48 | 55 | 12 | 14 | 11 |

| Colon Cancer | | | | |
|---|---|---|---|---|
| | SW480 | | HT29 | |
| Time (hr) | Control | Ketoconazole | Control | Ketoconazole |
| 0 | 0 | 0 | 0 | 0 |
| 24 | 40 | 27 | 18 | 8 |

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. Corner F I, Hart, G W, O-glycosylation of nuclear and cytosolic proteins: dynamic interplay between O-GlcNAc and O-phosphate. J. Biol. Chem. (2000) 275, 29179-29182.
2. Essentials of Glycobiology, 2nd edition. Edited by A Varki, R D Cummings, J D Esko, H H Freeze, P Stanley, C R Bertozzi, G W Hart, M E Etzler, Table 18.1, Cold Spring Harbor (NY): Cold Spring Harbor Laboratory Press (2009).
3. Noguchi K, Kitanaka C, Yamana H, Kokubu A, Mochizuki T, Kuchino Y, (November 1999). "Regulation of c-Myc through phosphorylation at Ser-62 and Ser-71 by c-Jun N-terminal kinase. J. Biol. Chem. (1999) 274, 32580-32587.
4. Yang W H, Kim J E, Nam H W, Ju J W, Kim H S, Modification of p53 with O-linked N-acetylglucosamine regulates p53 activity and stability. Nat. Cell Biol. (2006) 8, 1074-1083.
5. Chou T Y, Hart G W, Dang C V, c-Myc is glycosylated at threonine 58, a known phosphorylation site and a mutational hot spot in lymphomas J. Biol. Chem. (1995) 270, 18961-18965.
6. Kamemura K, Hart G W, Dynamic interplay between O-glycosylation and O-phosphorylation of nucleocytoplasmic proteins. J. Biol. Chem. (2002) 277, 19229-19235.
7. Dorfmueller, H C, van Aalten, D M F, Screening-based discovery of drug-like O-GlcNAcase inhibitor scaffolds. FEBS Letters (2010) 584, 694-700.

The invention claimed is:

1. A method of detecting or quantitating the expression of a site-specific O-GlcNAcylated protein expressed in cells and biological samples using a site-specific antibody to the site-specific O-GlcNAcylated protein, including the steps of:
   providing an O-GlcNAcylated target protein that is O-GlcNAcylated at a target O-GlcNAcylation site, or an O-GlcNAcylated target peptide thereof that is O-GlcNAcylated at the target O-GlcNAcylation site chosen from the group consisting of peptide 1G and peptide 2G, wherein the O-GlcNAcylated target protein is selected from the group consisting of p53 comprising an 0-GlcNAcylated Ser 149 and myc comprising an O-GlcNAcylated Thr-48, and wherein peptide 1G is a p53 peptide comprising O-GlcNacylated S149 and peptide 2G is myc peptide comprising O-GlcNAcylated Thr-48;
   providing a corresponding unmodified target protein that is not O-GlcNAcylated at the target O-GlcNAcylation site, or a corresponding unmodified target peptide thereof that is not O-GlcNAcylated at the target O-GlcNAcylation site chosen from the group consisting of peptide 1N and peptide 2N, wherein the O-GlcNAcylated target protein is selected from the group consisting of p53 comprising an unmodified Ser 149 and myc comprising an unmodified Thr-48, and wherein peptide 1G is a p53 peptide comprising an unmodified S149 and peptide 2G is myc peptide comprising an unmodified Thr-48;
   providing an O-GlcNAcylation site specificity control protein that is O-GlcNAcylated at a non-target O-GlcNAcylation site, or an O-GlcNAcylation site specificity control peptide thereof that is O-GlcNAcylated at the nontarget O-GlcNAcylation site chosen from the group consisting of an O-GlcNAcylated cmyc peptide and an O-GlcNAcylated p53 peptide;
   providing a corresponding unmodified site specificity control protein that is not O-GlcNAcylated at the non-target O-GlcNAcylation site, or an unmodified site specificity control peptide thereof that is not O-GlcNAcylated at the non-target O-GlcNAcylation site chosen from the group consisting of an unmodified cmyc peptide and an unmodified p53 peptide;
   providing a candidate site-specific antibody to the O-GlcNAcylated target protein;
   providing a candidate site-specific antibody to the unmodified target protein;
   reacting the candidate site-specific antibody to the O-GlcNAcylated target protein with the O-GlcNAcylated target protein or the O-GlcNAcylated target peptide; with the corresponding unmodified target protein or the unmodified target peptide; and with the O-GlcNAcylation site specificity control protein or the O-GlcNAcylation site specificity control peptide;
   reacting the candidate site-specific antibody to the unmodified target protein with the corresponding unmodified target protein or the unmodified target peptide; with the O-GlcNAcylated target protein or the O-GlcNAcylated target peptide; and with the corresponding unmodified site specificity control protein or the unmodified site specificity control peptide;
   determining that the candidate site-specific antibody to the O-GlcNAcylated target protein reacts specifically with the O-GlcNAcylated target protein or the O-GlcNAcylated target peptide, and does not cross-react with the corresponding unmodified target protein or the unmodified target peptide or with the O-GlcNAcylation site specificity control protein or the O-GlcNAcylation site specificity control peptide;
   determining that candidate site-specific antibody to the unmodified target protein reacts specifically with the corresponding unmodified target protein or the unmodified target peptide, and does not cross-react with the O-GlcNAcylated target protein or the O-GlcNAcylated target peptide, and does not cross-react with the corresponding unmodified site specificity control protein or the unmodified site specificity control peptide;
   characterizing the candidate antibody to the target O-GlcNAcylated peptide as a site-specific antibody to the O-GlcNAcylated target protein or the O-GlcNAcylated target peptide;
   characterizing the candidate site-specific antibody to the unmodified target protein as a site-specific antibody to the unmodified target protein or the unmodified target peptide;
   performing an immunoassay of the sample with the site-specific antibody to the site-specific O-GlcNAcylated protein; and
   measuring the expression of the site-specific O-GlcNAcylated protein in the sample.

2. The method of claim 1, additionally including the steps of performing an immunoassay of the sample with the site-specific antibody to an unmodified protein corresponding the site-specific O-GlcNAcylated protein; and
   measuring in the sample the expression of the unmodified protein corresponding the site-specific O-GlcNAcylated protein.

3. The method of claim 1 or claim 2, wherein the immunoassay is an ELISA assay, an immunoprecipitation assay, a chromatin immunoprecipitation assay, a Western Blot analysis, an immunofluorescence assay, or an immunohistochemical analysis.

4. The method of claim 1, wherein the site-specific antibody to the site-specific O-GlcNAcylated protein is a site-specific antibody to O-GlcNAcylated c-myc thereof;

the step of characterizing the candidate antibody to the O-GlcNAcylated target peptide as a site-specific antibody to the target O-GlcNAcylated protein or the O-GlcNAcylated target peptide is further defined as characterizing the candidate antibody as a site-specific antibody to, respectively, O-GlcNAcylated c-myc protein and an O-GlcNAcylated c-myc peptide.

5. The method of claim 2, wherein the site-specific antibody to the unmodified site-specific protein is a site-specific antibody to unmodified c-myc thereof;

the step of characterizing the candidate site-specific antibody to the unmodified target protein as a site-specific antibody to the unmodified target protein or the unmodified target peptide is further defined as characterizing the candidate antibody as a site-specific antibody to, respectively, unmodified c-myc protein and an unmodified c-myc peptide.

6. The method of claim 2, wherein the step of obtaining a sample is further defined as obtaining the cytosolic fraction of a population of cells; wherein the antibody to the site-specific O-GlcNAcylated protein is a site-specific antibody to O-GlcNAcylated p53, as characterized by the method of claim 1; and wherein the antibody to the site-specific unmodified protein is a site-specific antibody to unmodified p53, as characterized by the method of claim 1.

7. The method of claim 4 or 5, wherein the step of obtaining a sample is further defined as obtaining the nuclear fraction of a population of cells, wherein the antibody to the site-specific O-GlcNAcylated protein is a site-specific antibody to O-GlcNAcylated c-myc and wherein the antibody to the site-specific unmodified protein is a site-specific antibody to unmodified c-myc thereof;

the step of characterizing the candidate antibody to the O-GlcNAcylated target peptide as a site-specific antibody to the target O-GlcNAcylated protein or the O-GlcNAcylated target peptide is further defined as characterizing the candidate antibody as a site-specific antibody to, respectively, O-GlcNAcylated c-myc protein and an O-GlcNAcylated c-myc peptide; and the step of characterizing the candidate site-specific antibody to the unmodified target protein as a site-specific antibody to the unmodified target protein or the unmodified target peptide is further defined as characterizing the candidate antibody as a site-specific antibody to, respectively, unmodified c-myc protein and an unmodified c-myc peptide.

\* \* \* \* \*